US008037740B2

(12) United States Patent
Fujii (10) Patent No.: US 8,037,740 B2
(45) Date of Patent: Oct. 18, 2011

(54) CONDUCTIVE MATERIAL CONCENTRATION MEASURING DEVICE AND MAGNETIC MATERIAL CONCENTRATION MEASURING DEVICE

(75) Inventor: Takashi Fujii, Aioi (JP)

(73) Assignee: Diesel United, Ltd., Tokyo (JP)

( * ) Notice: Subject to any disclaimer, the term of this patent is extended or adjusted under 35 U.S.C. 154(b) by 478 days.

(21) Appl. No.: 12/297,451

(22) PCT Filed: Apr. 26, 2007

(86) PCT No.: PCT/JP2007/000461
§ 371 (c)(1),
(2), (4) Date: Oct. 17, 2008

(87) PCT Pub. No.: WO2007/129462
PCT Pub. Date: Nov. 15, 2007

(65) Prior Publication Data
US 2009/0100913 A1    Apr. 23, 2009

(30) Foreign Application Priority Data
Apr. 28, 2006   (JP) .................. 2006-124883

(51) Int. Cl.
*G01N 27/72* (2006.01)
(52) U.S. Cl. ....... 73/61.42; 73/61.41; 324/204; 324/228
(58) Field of Classification Search .......... 73/61.41, 73/61.42; 324/204, 228
See application file for complete search history.

(56) References Cited

U.S. PATENT DOCUMENTS

| 4,243,059 | A |   | 1/1981  | Hammon et al. |
|-----------|---|---|---------|----------------|
| 4,267,722 | A | * | 5/1981  | Hendry ............................ 73/10 |
| 4,646,070 | A |   | 2/1987  | Yasuhara et al. |
| 4,677,425 | A | * | 6/1987  | Singleton ..................... 340/627 |
| 4,686,469 | A | * | 8/1987  | Lewis .......................... 324/204 |
| 5,038,893 | A | * | 8/1991  | Willner et al. ................. 184/7.4 |
| 5,089,780 | A | * | 2/1992  | Megerle ....................... 324/448 |
| 5,384,535 | A | * | 1/1995  | Mayeur ........................ 324/204 |
| 5,572,320 | A | * | 11/1996 | Reintjes et al. .............. 356/335 |
| 5,619,333 | A | * | 4/1997  | Staff et al. .................... 356/436 |
| 5,754,055 | A |   | 5/1998  | McAdoo et al. |
| 5,964,318 | A | * | 10/1999 | Boyle et al. ................... 184/1.5 |

FOREIGN PATENT DOCUMENTS

| JP | 8 201245    | 8/1996  |
|----|-------------|---------|
| JP | 10 268013   | 10/1998 |
| JP | 2001-153844 | 6/2001  |
| JP | 2004 333280 | 11/2004 |
| JP | 2005 83897  | 3/2005  |
| JP | 2005 299459 | 10/2005 |
| JP | 2006-317251 | 11/2006 |

* cited by examiner

*Primary Examiner* — David A. Rogers
(74) *Attorney, Agent, or Firm* — Oblon, Spivak, McClelland, Maier & Neustadt, L.L.P.

(57) ABSTRACT

A detection unit 4 with detection means 3 and fluid inflow/outflow guide means 2 is connected to a passage 1 for fluid with conductive material or to a pool section 5 for pooling of the fluid. The detection unit 4 guides inflow and outflow of the fluid through the fluid inflow/outflow guide means 2 and detects a concentration of conductive material through the detection means 4. A concentration of conductive material in the fluid is continuously measured with high accuracy.

12 Claims, 7 Drawing Sheets

CONDUCTIVE MATERIAL CONCENTRATION MEASURING DEVICE AND MAGNETIC MATERIAL CONCENTRATION MEASURING DEVICE

TECHNICAL FIELD

The present invention relates to a conductive material concentration measuring device and a magnetic material concentration measuring device.

BACKGROUND ART

In an engine or other prime mover with a piston or other reciprocating part, for example, the piston and a cylinder may wear due to sliding motions between them, resulting in production of iron powder or other magnetic material which is entrained in drain oil from the engine flowing through a passage. Thus, it is required to measure a concentration of the magnetic material contained in order to accurately grasp worn degree of the equipment.

Generally, in order to grasp the worn degree of the equipment, lubricant or drain oil is manually sampled to measure a concentration of magnetic material; alternatively, a magnetic material concentration measuring device is arranged adjacent to the passage for the lubricant or drain oil to measure the concentration of magnetic material.

A magnetic material concentration measuring device comprises, for example, an observational LC oscillation circuits with a first coil adjacent to a passage for drain oil and a corrective LC oscillation circuit with a second coil arranged in a position not affected by the magnetic material in the drain oil, the concentration of the magnetic material being detected on the basis of difference in oscillating frequency between the LC oscillation circuits (see, for example, Patent Literature 1). Another example comprises magnetic-field applying means and magnetic measuring means with a magnetic sensor in the form of a superconducting quantum interference device both arranged adjacent to a passage for drain oil so as to detect only magnetic fields of magnetized components, which has been disclosed for example in the latter:

[Patent Literature 1] JP 2005-83897A
[Patent Literature 2] JP 10-268013A

SUMMARY OF INVENTION

Technical Problems

However, the manual sampling of the fluid such as lubricant or drain oil to measure the concentration of magnetic material is troublesome and is disadvantageous in that measurement can be effected only in a constant interval, resulting in possibly delayed detection of abnormality in the equipment. In the case of using a conventional magnetic material concentration measuring device, varied flow rate of the fluid may cause air to stay in the passage and/or may cause solid bodies to be accumulated, disadvantageously resulting in failure of continuous measurement with high accuracy. In order to remove the accumulated solid bodies, periodical air blowing or mechanical removal has been conducted, which is troublesome and may cause further accumulation due to aged deterioration. Replacement of the fluid through natural circulation or drop is much time-consuming especially in the case of the fluid with high viscosity, disadvantageously resulting in failure of continuous measurement and leading to delayed detection of abnormality in the equipment.

The invention was made in view of the above and has its object to provide a conductive material concentration measuring device for continuously measuring concentration of conductive material in fluid with high accuracy and provide a magnetic material concentration measuring device for continuously measuring concentration of magnetic material in fluid with high accuracy.

Solution to Problems

The invention is directed to a conductive material concentration measuring device comprising a detection unit with detection means and fluid inflow/outflow guide means, said detection unit being connected to a passage for the fluid or to a pool section for pooling of the fluid, said detection unit guiding inflow and outflow of the fluid through said fluid inflow/outflow guide means and detecting a concentration of the conductive material through said detection means.

In the invention, preferably, the detection unit is connected to the pool section such that air is prevented from interfusing.

In the invention, preferably, the pool section comprises first and second pool sections for pooling of old and new fluids, respectively, said detection unit being connected to the second pool section.

In the invention, preferably, said pool section is formed in the passage through shutoff means.

Thus, according to the invention, guided flow of the fluid into and out of the detection unit is facilitated since the guided inflow and outflow of the fluid is conducted by the fluid inflow/outflow guide means; the concentration of the conductive material in the fluid is continuously measured with high accuracy since the concentration is detected by the detection unit different in pathway from the passage. As a result, any abnormality in the equipment can be quickly detected. Movements of the fluid inflow/outflow guide means, which remove any accumulated solid and other bodies, makes it unnecessary to conduct periodic air blowing or mechanical removal and prevents further accumulation from occurring, so that the concentration of conductive material in the fluid can be continuously measured with high accuracy. Even if the fluid has higher viscosity, the inflow and outflow of the fluid can be surely guided by the fluid inflow/outflow guide means in a constant interval, so that the concentration of conductive material in the fluid can be continuously measured with high accuracy.

The invention is directed to a magnetic material concentration measuring device comprising a detection unit with detection means and a piston, said detection unit being connected to a passage for fluid with magnetic material, said detection unit guiding inflow and outflow of the fluid through said piston and detecting a concentration of magnetic material through said detection means.

In the invention, preferably, the detection unit is connected to the pool section for pooling of the fluid such that air is prevented from interfusing.

In the invention, preferably, the pool section comprises first and second pool sections for pooling of old and new fluids, respectively, the detection unit being connected to the second pool section.

In the invention, preferably, the pool section is formed in the passage through shutoff means.

Thus, according to the invention, guided flowing of the fluid into and out of the detection unit is conducted by reciprocal movements of the piston, which facilitates replacement of the fluid in the detection unit; and a concentration of the magnetic material in the fluid is continuously measured with high accuracy since the concentration is detected by the detection unit different in pathway from the passage. As a result, abnormality in the equipment can be quickly detected. Reciprocal movements of the piston, which remove accumulated solid and other bodies, makes it unnecessary to conduct periodic air blowing or mechanical removal and prevents further accumulation from occurring, so that the concentration of magnetic material in the fluid can be continuously measured with high accuracy. Even if the fluid has higher viscosity, the inflow and outflow of the fluid can be surely guided by the reciprocal movements of the piston in a constant interval, so that the concentration of the magnetic material in the fluid can be continuously measured with high accuracy.

In the invention, when the detection unit is connected to the pool section in the passage for pooling of the fluid such that air is prevented from interfusing, guided inflow and outflow of the fluid is conducted by piston or other fluid inflow/outflow guide means without interfusion of air into the detection unit, so that replacement of the fluid in the detection unit can be facilitated and the concentration of conductive material (or magnetic material) in the fluid can be continuously measured with high accuracy. Since the detection unit is connected to the pool section, interfusion of air can be prevented by vibrations and the like of the equipment.

In the invention, when the pool section comprises first and second pool sections for pooling of old and new fluids, respectively, and the detection unit is connected to the second pool section, then the new fluid is guided into the detection unit by the piston or other fluid inflow/outflow guide means, so that the old and new fluids are prevented from being mixed together and the concentration of conductive material (or magnetic material) in the fluid can be continuously measured with high accuracy.

In the invention, when the pool section is formed in the passage through the shutoff means, the pool section is easily formed in the passage, so that replacement of the fluid in the detection unit is easily conducted and the concentration of conductive material (or magnetic material) in the fluid can be continuously measured with high accuracy.

Advantageous Effects of Invention

Various excellent effects and advantages can be obtained according to the invention. By the detection unit with the fluid inflow/outflow guide means, the concentration of conductive material (or magnetic material) in the fluid can be continuously measured with high accuracy to quickly detect abnormality in the equipment. Moreover, by the detection unit with the piston, the concentration of conductive material (or magnetic material) in the fluid can be continuously measured with high accuracy to quickly detect abnormality in the equipment.

REFERENCE SIGNS LIST

1 passage
2 piston (fluid inflow/outflow guide means)
3 detection means
4 detection unit
5 pool section
6 on-off valve (shutoff means)
11 detection body (fluid inflow/outflow guide means)
21 passage
23 on-off valve (shutoff means)
29 first pool section
30 second pool section
30*a* second pool section
31 passage
35 on-off valve (shutoff means)
39 first pool section
40 second pool section
41 passage
42 rotator (fluid inflow/outflow guide means)
43 detection means
44 detection unit
49 on-off valve (shutoff means)
54 first pool section
55 second pool section
56 detection body (fluid inflow/outflow guide means)
60 detection unit
62 detection body (fluid inflow/outflow guide means)
64 rotator (fluid inflow/outflow guide means)
65 detection means

DESCRIPTION OF EMBODIMENTS

Figure 1:
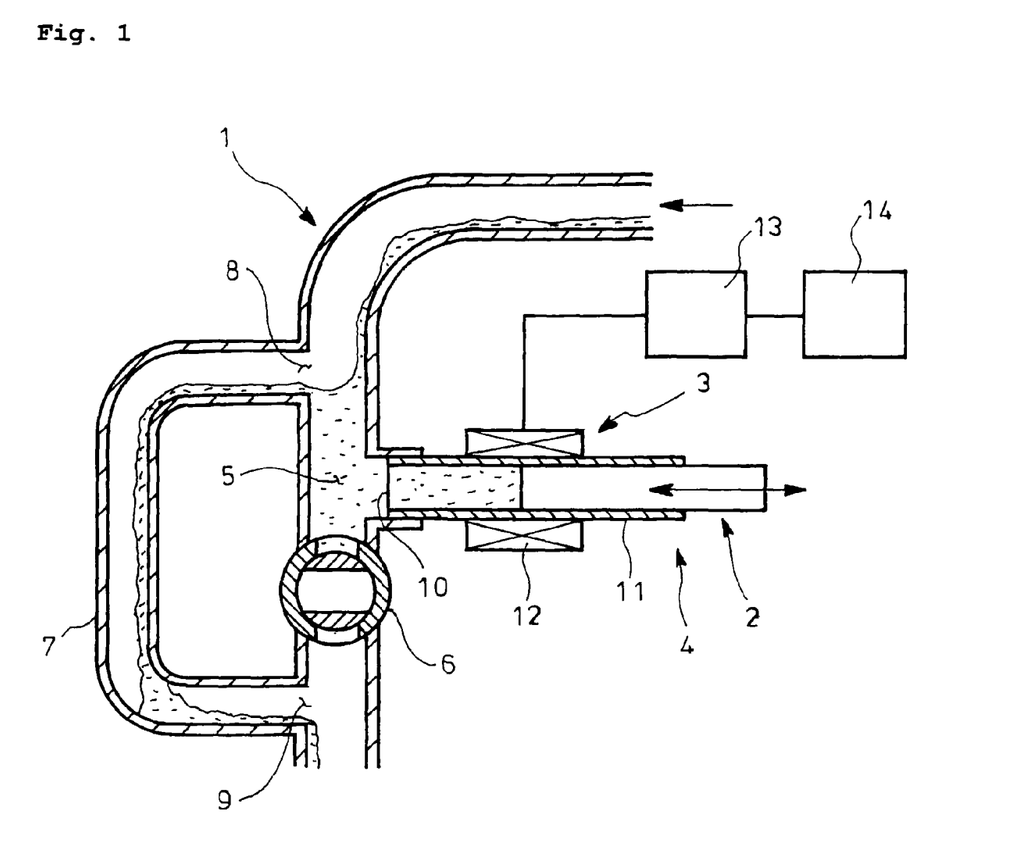
FIG. 1 is a schematic view showing a first embodiment of the invention.

A conductive material concentration measuring device according to a first embodiment of the invention will be described which is constituted as a magnetic material concentration measuring device for measuring a concentration of magnetic material powder included in lubricant. The first embodiment of the invention is schematically shown in FIG. 1.

In the measuring device of the first embodiment, connected to a conduit passage 1 for passage of fluid such as lubricant including conductive material is a detection unit 4 having a piston (fluid inflow/outflow guide means) 2 and detection means 3. The conductive material is not limited to magnetic material such as iron, cobalt or nickel and may be non-magnetic material such as aluminum, copper or stainless-steel, provided that it has electrical conductivity. The fluid is not limited to lubricant or drain oil and may be any, provided that it contains conductive material.

The conduit passage 1 is for inflow and outflow of the lubricant into and out of an equipment (not shown) with sliding parts or components. Arranged downstream of the passage 1 are an on-off valve 6 as shutoff means which forms a pool section 5 for the lubricant and a branch passage 7 for bypassing the valve 6. The branch passage 7 has a branch port 8 upstream of the pool section 5 and a junction port 9 downstream of the on-off valve 6 and serves to cause the overflowing lubricant from the pool section 5 to flow downstream. The sliding parts or components are not limited to a drive piston and a drive cylinder and may be any, provided that they may slide.

The detection unit 4 comprises a cylindrical detection body (fluid inflow/outflow guide means) 11 with an opening 10 to the pool section 5 so as to be arranged for the passage 1 between the on-off valve 6 and the branch port 8, a piston (fluid inflow/outflow guide means) 2 slidable in the detection body 11, drive means (not shown) for driving the piston 2, a sensor 12 in the detection means 3 arranged on an outer periphery of the detection body 11, a signal processing circuit 13 in the detection means 3 for control of the sensor 12 and a measured value indicating and abnormality determination device 14 connected to the circuit 13.

The sensor 12 in the detection means 3 measures the concentration of the magnetic material powder through, for example, differential transformer type detection; however, the way of detection is not limited thereto and may be any, provided that it can measure a concentration of magnetic material powder.

Mode of operation of the first embodiment according to the invention will be described.

Upon measurement the concentration of the magnetic material powder included in the lubricant (fluid), with the piston 2 in the detection unit 4 being preliminarily pushed out, the on-off valve 6 in the passage 1 is closed to pool a constant amount of lubricant in the pool section 5. Whether the predetermined amount of lubricant has been pooled or not in the pool section 5 may be determined on the basis of lapse of a predetermined time; alternatively, it may be determined on the basis of detection of the overflowing lubricant into the branch passage 7 as shown in FIG. 1; alternatively, any other determination means may be employed.

Then, the piston 2 as the fluid inflow/outflow guide means is withdrawn to guide the lubricant in the pool section 5 into the detection unit 4 and the concentration of magnetic material powder in the lubricant is measured by the sensor 12 in the detection means 3. The detection means 3 measures an output signal from the sensor 12 via the signal processing circuit 13. Since the output signal from the sensor 12 varies depending on the concentration of magnetic material powder in the detection unit 4, the concentration of magnetic material powder is measured through functional processing of the output signal from the sensor 12 or through contrast processing using correlation of the concentration of the magnetic material powder.

Then, the piston 2 as fluid inflow/outflow guide means is pushed out to discharge (guide the outflow of) the lubricant in the detection unit 4 into the pool section 5 so that the accumulated bodies in the detection unit 4 are discharged and the lubricant in the detection unit 4 and the pool section 5 is replaced.

With such reciprocal movements of the piston 2 being continued, the concentration of magnetic material powder in the lubricant is continuously measured. When the concentration of magnetic material powder exceeds the predetermined value, the fact is regarded to be a sign of the equipment with the sliding parts or components being considerably worn and needing maintenance, so that the measured value indicating and abnormality determination device 14 announces it to an administrator by way of warning display, beep and/or light. Time interval of the reciprocal movements of the piston 2, which may vary depending on, for example, viscosity of the fluid to be measured, is preferably on the order of several seconds or several tens of seconds.

Thus, according to the first embodiment, the reciprocal movements of the piston (fluid inflow/outflow guide means) 2 facilitate inflow and outflow and replacement of the fluid such as lubricant in the detection unit 4, so that the replacement of the lubricant in the detection unit 4 is accelerated. Since the concentration of magnetic material powder in the fluid is stably detected in the detection unit 4 different in pathway from the passage 1, the concentration of magnetic material powder in the fluid is continuously measured with high accuracy. As a result, abnormality in the equipment can be quickly detected. Since the abnormality of the sliding parts in the equipment can be quickly detected, maintenance can be made before the equipment suffers from serious damages. Moreover, since the concentration of the magnetic material powder is detected in the detection unit 4 different in pathway from the passage 1, the detection can be prevented from being affected by disturbances such as magnetic noise, electromagnetic noise, temperature variation and electric noise.

Since the accumulated solid and other bodies are removed by reciprocating the piston 2, a periodic air blowing or mechanical removal becomes unnecessary and occurrence of further accumulation or change in measurement conditions is prevented, so that the concentration of magnetic material powder in the fluid can be continuously measured with high accuracy. Even if the fluid has high viscosity, inflow and outflow of the fluid can be surely guided in a constant interval by reciprocating the piston 2, so that the concentration of magnetic material powder in the fluid can be continuously measured with high accuracy. The reciprocal movements of the piston 2 easily discharge air originally existing in the passage 1 and the detection unit 4, so that movement of the fluid becomes smooth and the concentration of magnetic material powder in the fluid can be continuously measured with high accuracy.

In an equipment such as diesel engine, lubricant is fed with revolution speed and charged fuel degree as parameters; supply of the lubricant may be also controlled with the measured concentration of magnetic material powder in the lubricant used as condition parameter for a drive cylinder (cylinder liner). When, in addition to measurement of the concentration of magnetic material, means is provided for measurement of an amount of the drain oil, a worn amount of the equipment can be estimated so that timing for maintenance of the equipment can be properly grasped to reduce time and cost required for the maintenance.

In the first embodiment, when the detection unit 4 is connected to the pool section 5 for pooling of the fluid in the passage 1 such that air is prevented from interfusing, inflow and outflow of the fluid is guided by the piston 2 as fluid inflow/outflow guide means without interfusion of air into the detection unit 4, so that the replacement of the fluid in the detection unit 4 can be easily conducted and the concentration of magnetic material powder in the fluid can be continuously measured with high accuracy. Since the detection unit 4 is connected to the pool section 5, air is prevented from interfusing by vibrations and the like of the equipment such as engine. Even if the fluid has high viscosity, inflow and outflow of the fluid into and out of the pool section 5 can be favorably guided in a constant interval by reciprocal movements of the piston 2, so that the concentration of magnetic material powder in the fluid can be continuously measured with high accuracy.

In the first embodiment, when the pool section 5 is formed in the passage 1 through the on-off valve 6 as shutoff means, the pool section 5 is easily formed in the passage 1, so that replacement of the fluid in the detection unit 4 can be easily conducted and the concentration of magnetic material powder in the fluid can be continuously measured with high accuracy. Even if the fluid has high viscosity, inflow and outflow of the fluid into and out of the pool section 5 can be favorably guided in a constant interval by reciprocal movements of the piston 2 as fluid inflow/outflow guide means, so that the concentration of magnetic material powder in the fluid can be continuously measured with high accuracy.

Figure 2:
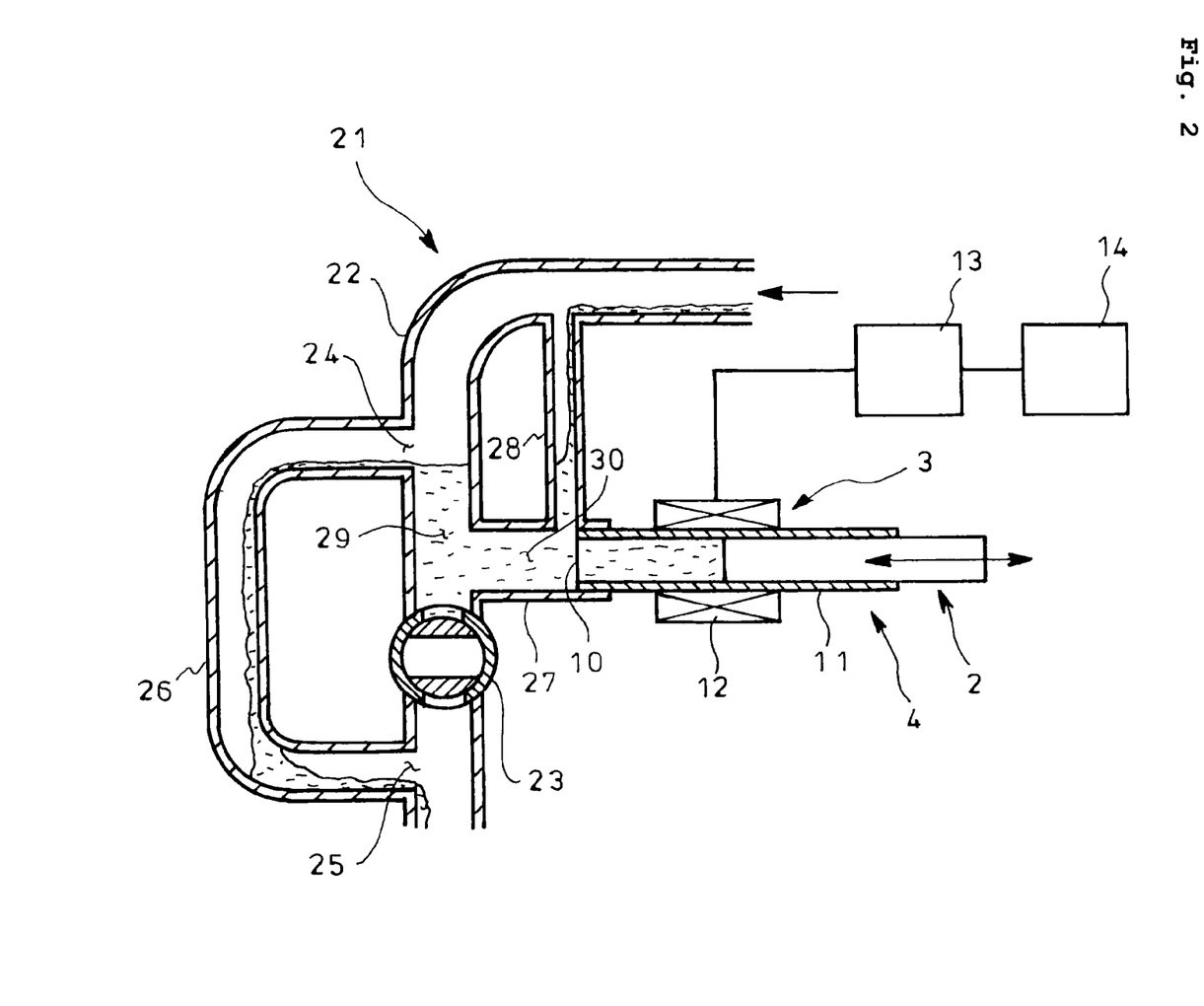
FIG. 2 is a schematic view showing a second embodiment of the invention.
Figure 3:
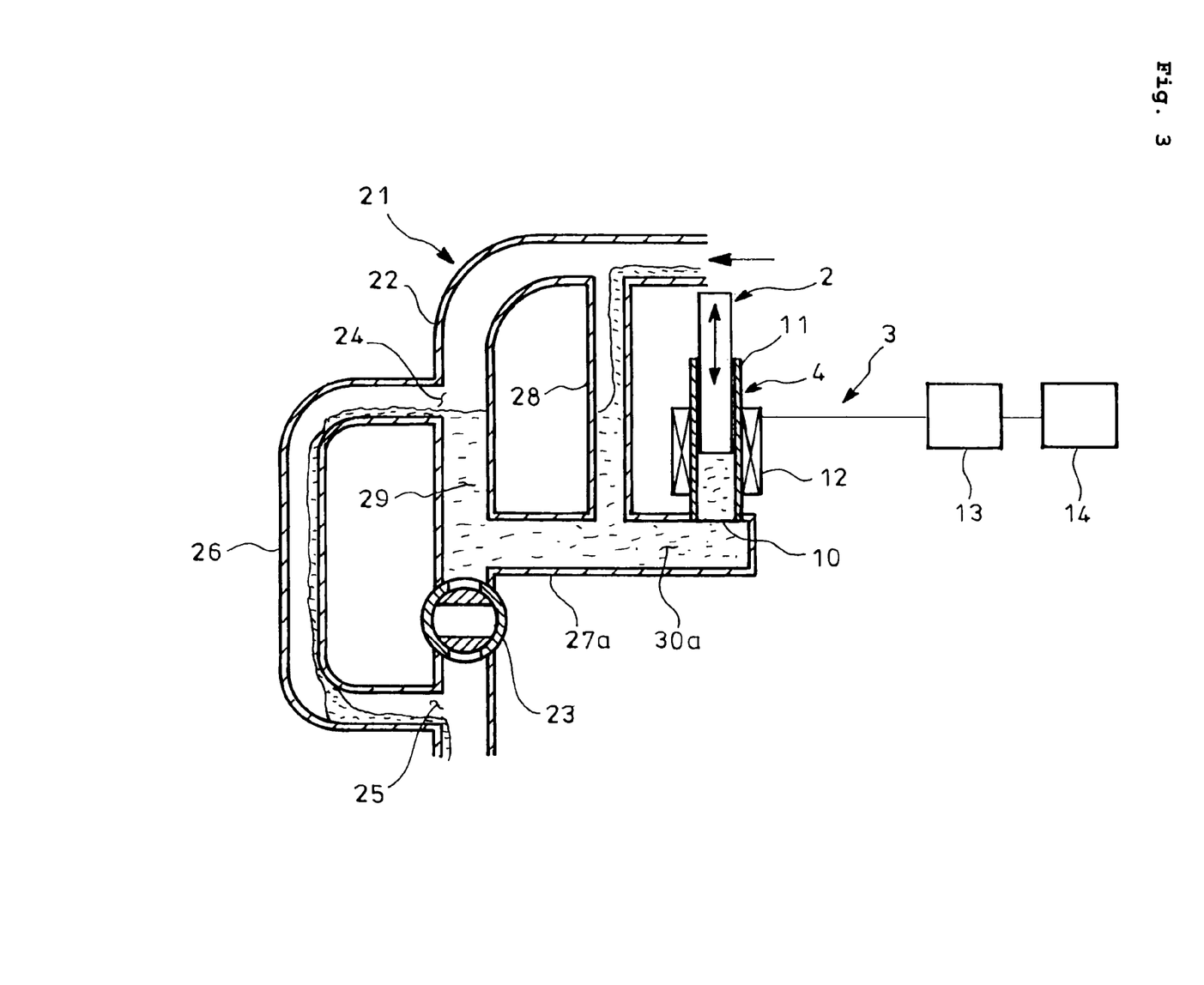
FIG. 3 is a schematic view showing a variation of the second embodiment of the invention.

Next, a conductive material concentration measuring device according to a second embodiment of the invention will be described which is constituted, just like the first embodiment, as a magnetic material concentration measuring device for measuring a concentration of magnetic material powder included in lubricant. FIG. 2 is a schematic view showing the second embodiment of the invention and FIG. 3 is a schematic view showing a variation of the second embodiment of the invention. In the figures, parts similar to those in FIG. 1 are represented by the same reference numerals.

The measuring device of the second embodiment has a variation of the passage 1, i.e., a passage 21 for the fluid such as lubricant including conductive material to which is connected a detection unit 4 just like the first embodiment. The conductive material is not limited to magnetic material such as iron, cobalt or nickel and may be non-magnetic material such as aluminum, copper or stainless-steel, provided that it has electric conductivity. The fluid is not limited to lubricant or drain oil and may be any, provided that it contains conductive material.

The passage 21 of the second embodiment is for discharge of the lubricant from an equipment (not shown) with sliding parts or components. Downstream of the passage 21 are a main passage 22 extending curvedly from horizontal to vertical, an on-off valve 23 as shutoff means arranged in the vertical portion of the main passage 22, a branch passage 26 arranged to bypass the on-off valve 23 and having, just like the first embodiment, a branch port 24 and a junction port 25, an extension passage 27 at a position between the on-off valve 23 and the branch port 24 and extending horizontally for a predetermined length, and a small-diameter communication passage 28 for connecting an end of the passage 27 with the horizontal portion of the main passage 22. The sliding parts or components are not limited to a drive piston and a drive cylinder and may be any, provided that they may slide.

The main passage 22 from the branch port 24 to the on-off valve 23 as shutoff means provides a first pool section 29 for the old fluid or lubricant, and the extension and communication passages 27 and 28 provide a second pool section 30 for receiving the new fluid or lubricant to pool the same. Like the first embodiment, the branch passage 26 serves to cause the overflowing lubricant from the first pool section 29 to flow downstream. The communication passage 28 is arranged such that the lubricant flows sooner therethrough than through the vertical portion of the main passage 22.

The detection unit 4 comprises a cylindrical detection body (fluid inflow/outflow guide means) 11 with an opening 10 to the second pool section 30 so as to be arranged at a junction between the extension passage 27 and the communication passage 28, a piston (fluid inflow/outflow guide means) 2 slidable in the detection body 11, drive means (not shown) for driving the piston 2, a sensor 12 in the detection means 3 arranged on an outer periphery of the detection body 11, a signal processing circuit 13 for control of the sensor 12 in the detection means 3 and a measured value indicating and abnormality determination device 14 connected to the circuit 13. For enhanced certainty of guiding the fluid, it is preferable that the detection body 11 in the detection unit 4 is arranged to extend from an end of the extension passage 27.

Just like the first embodiment, the sensor 12 in the detection means 3 measures the concentration of the magnetic material powder through, for example, differential transformer type detection; however, the way of detection is not limited thereto and may be any, provided that it can measure a concentration of magnetic material powder.

The conductive material concentration measuring device of the second embodiment has a variation as shown in FIG. 3 comprising an extension passage 27a extending from between the on-off valve 23 and the branch port 24 horizontally for a predetermined length and a communication passage 28 and a small-diameter communication passage 28 for connecting an intermediate portion of the extension passage 27a with the horizontal portion of the main passage 22, said extension passage 27a and communication passage 28 providing the second pool section 30a for receiving and pooling the new fluid or lubricant.

The detection unit 4 of the variation comprises a cylindrical detection body (fluid inflow/outflow guide means) 11 with an opening 10 to the second pool section 30 so as to be arranged above an end of the extension passage 27, a piston (fluid inflow/outflow guide means) 2 vertically slidable in the detection body 11, drive means (not shown) for driving the piston 2, a sensor 12 in the detection means 3 arranged on an outer periphery of the detection body 11, a signal processing circuit 13 in the detection means 3 for controlling the sensor 12 and a measured value indicating and abnormality determination device 14 connected to the circuit 13.

As shown in FIG. 3, the remaining portions of the variation are substantially similar to those in the second embodiment.

Mode of operation of the second embodiment will be described.

Upon measurement of the concentration of magnetic material power included in the lubricant, with the piston 2 in the detection unit 4 being preliminarily pushed out, the on-off valve 23 in the conduit main passage 22 is closed to pool a constant amount of lubricant in the first and second pool sections 29 and 30. Whether a predetermined amount of lubricant has been pooled or not in the second pool section 30 may be determined on the basis of lapse of a predetermined time; alternatively, it may be determined on the basis of detection of the overflowing lubricant into the branch passage 26 as shown in FIG. 2; alternatively, any other determination means may be employed.

Then, the piston 2 as fluid inflow/outflow guide means is withdrawn to guide the lubricant in the second pool section 30 into the detection unit 4 and the concentration of magnetic material powder in the lubricant is measured by the sensor 12 in the detection means 3. The detection means 3 measures an output signal from the sensor 12 via the signal processing circuit 13. Since the output signal from the sensor 12 varies depending on the concentration of magnetic material powder in the detection unit 4, the concentration of magnetic material powder is measured through functional processing of the output signal from the sensor 12 or through contrast processing using correlation of the magnetic material powder.

Then, the piston 2 as fluid inflow/outflow guide means is pushed out to discharge (or guide the outflow of) the lubricant in the detection unit 4 into the second pool section 30, so that the accumulated bodies in the detection unit 4 are discharged and the lubricant in the detection unit 4 and the second pool section 30 is replaced. The lubricant discharged from the detection unit 4 into the second pool section 30 is discharged into the branch passage 26 via the first pool section 29.

Further, with the piston 2 as fluid inflow/outflow guide means being withdrawn, new lubricant flows via the communication passage 28 into and stays in the second pool section 30. Thus, with the new lubricant being introduced, the concentration of magnetic material powder in the lubricant is measured by the sensor 12 in the detection means 3.

Then, with such reciprocal movements of the piston 2 being continued, the concentration of magnetic material powder in the lubricant is continuously measured. When the concentration of magnetic material powder exceeds the predetermined value, the fact is regarded to be a sign of the equipment with the sliding parts or components being considerably worn and needing maintenance, so that the measured value indicating and abnormality determination device 14 announces it to an administrator by way of warning display, beep and/or light. Time interval of the reciprocal movements of the piston 2, which may vary depending upon, for example, viscosity of the fluid, is preferably on the order of several seconds or several tens of seconds.

In the variation of the second embodiment, for introduction of the lubricant in second pool section 30a into the detection unit 4, the piston 2 as fluid inflow/outflow guide means is withdrawn to upwardly introduce and suck the lubricant in the second pool section 30a into the detection unit 4; when the lubricant in the detection unit 4 is discharged (guided) into the second pool section 30a, the piston 2 as fluid inflow/outflow guide means is pushed out to discharge the lubricant in the detection unit 4 downwardly into the second pool section 30a. The other treatments are utterly the same as those in the second embodiment.

Thus, according to the second embodiment, the effects and advantages can be obtained which are substantially same as those of the first embodiment.

In the second embodiment wherein the pool section comprises the first and second pool sections 29 and 30 for pooling and storage of the old and new fluids, respectively, the detection unit 4 being connected to the second pool section 30, the new fluid or lubricant is introduced into the detection unit 4 by the piston 2, so that mixing of the old fluid with the new fluid is prevented and the concentration of magnetic material in the fluid can be continuously measured with high accuracy. Due to the arrangement of the detection unit 4 and due to the first and second pool sections 29 and 30, interfusion of air into the fluid is favorably prevent, so that the concentration of magnetic material powder in the fluid can be measured continuously and with extremely high accuracy. Since the detection unit 4 is connected to the second pool section 30, interfusion of air can be prevented by vibrations and the like of the equipment such as engine.

Further, in the variation of the second embodiment with the detection unit 4 being arranged above the second pool section 30a so as to direct the piston 2 downward, accumulation of solid and other bodies (sludge) in the detection unit 4 can be further favorably prevented.

Figure 4:
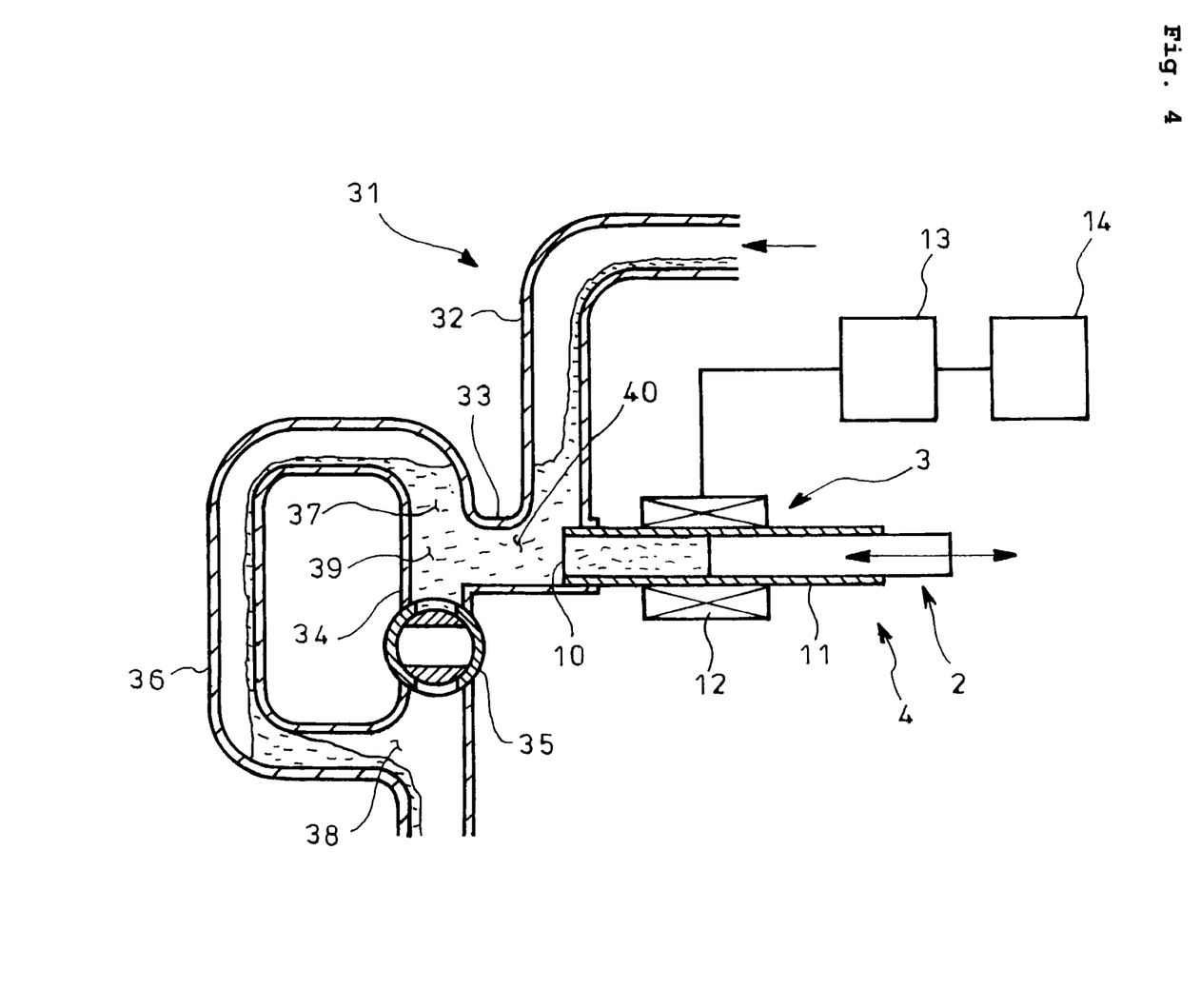
FIG. 4 is a schematic view showing a third embodiment of the invention.

Next, a conductive material concentration measuring device according to a third embodiment of the invention will be described which is, just like the first embodiment, constituted as a magnetic material concentration measuring device for measuring a concentration of magnetic material powder included in lubricant. FIG. 4 is a schematic view showing the third embodiment of the invention. In the figure, parts similar to those in FIG. 1 are represented by the same reference numerals.

The measuring device of the third embodiment has a further variation of the conduit passage 1, i.e., a passage 31 for the fluid such as lubricant including conductive material to which is connected a detection unit 4 just like the first embodiment. The conductive material is not limited to magnetic material such as iron, cobalt or nickel and may be non-magnetic material such as aluminum, copper or stainless-steel, provided that it has electrical conductivity. The fluid is not limited to lubricant or drain oil and may be any, provided that it contains conductive material.

The conduit passage 31 of the third embodiment is for discharge of the lubricant from an equipment (not shown) with sliding parts or components. Downstream of the passage 31 are a first passage 32 extending curvedly from horizontal to vertical, an intermediate passage 33 extending from the first passage 32 curvedly into horizontal, a second passage 34 extending from the intermediate passage 33 curvedly into vertical, an on-off valve 35 as shutoff means in the second passage 34 and a branch passage 36 arranged for the second passage 34 to bypass the on-off valve 35 and having a branch port 37 at the other end of the intermediate passage 33 and a junction port 38 downstream of the on-off valve 35. The sliding parts or components are not limited to a drive piston and a drive cylinder and may be any, provided that they may slide.

The second passage 34 from a halfway position of the intermediate passage 33 to the on-off valve 35 as shutoff means provides a first pool section 39 for pooling of the old fluid or lubricant, and a portion from the first passage 32 to the halfway position of the intermediate passage 33 provides a second pool section 40 for receiving and pooling of the new fluid or lubricant. The branch passage 36 serves to cause the overflowing lubricant from the first pool section 39 to flow downstream.

The detection unit 4 comprises a cylindrical detection body (fluid inflow/outflow guide means) 11 with an opening 10 to the second pool section 40 so as to be arranged at a junction between the intermediate passage 33 and the first passage 32, a piston (fluid inflow/outflow guide means) 2 slidable in the detection body 11, drive means (not shown) for driving the piston 2, a sensor 12 in the detection means 3 arranged on an outer periphery of the detection body 11, a signal processing circuit 13 in the detection means 3 for control of the sensor 12 and a measured value indicating and abnormality determination device 14 connected to the circuit 13. For enhanced certainty of guiding the fluid, it is preferable that the detection body 11 in the detection unit 4 is arranged to extend from an end of the intermediate passage 33.

Just like the first embodiment, the sensor 12 in the detection means 3 measures the concentration of magnetic material power through, for example, differential transformer type detection; however, the way of detection is not limited thereto and may be any, provided that it can measure a concentration of magnetic material powder. Like the variation of the second embodiment, the second pool section 40 may be extended to arrange the detection unit 4 above the second pool section 40.

Mode of operation of the third embodiment will be described.

Upon measurement of the concentration of magnetic material powder included in the lubricant, with the piston 2 in the detection unit 4 being preliminarily pushed out, the on-off valve 35 in the passage 31 is closed to pool a constant amount of lubricant in the first and second pool sections 39 and 40. Whether a predetermined amount of lubricant has been pooled or not in the second pool section 40 may be determined on the basis of lapse of a predetermined time; alternatively, it may be determined on the basis of detection of the overflowing lubricant into the branch passage 36 as shown in FIG. 4; alternatively, any other determination means may be employed.

Then, the piston 2 as fluid inflow/outflow guide means is withdrawn to guide the lubricant in the second pool section 40 into the detection unit 4 and the concentration of magnetic material powder in the lubricant is measured by the sensor 12 in the detection means 3. The detection means 3 measures an output signal from the sensor 12 via the signal processing circuit 13. Since the output signal from the sensor 12 varies depending on the concentration of the magnetic material powder in the detection unit 4, the concentration of magnetic material powder is measured through functional processing of the output signal from the sensor 12 or through contrast processing using correlation of magnetic material powder.

Then, the piston 2 as fluid inflow/outflow guide means is pushed out to discharge (or guide the outflow of) the lubricant in the detection unit 4 into the second pool section 40, so that the accumulated bodies in the detection unit 4 are discharged and the lubricant in the detection unit 4 and the second pool section 40 is replaced. The lubricant discharged from the detection unit 4 into the second pool section 40 is discharged into the branch passage 36 via the first pool section 39.

Further, with the piston 2 as fluid inflow/outflow guide means being withdrawn, new lubricant flows via the first passage 32 into and stays in the second pool section 40. Thus, with the new lubricant being introduced, the concentration of magnetic material powder in the lubricant is measured by the sensor 12 in the detection means 3.

Then, with such reciprocal movements of the piston 2 being continued, the concentration of magnetic material powder in the lubricant is continuously measured. When the concentration of magnetic material powder exceeds a predetermined value, the fact is regarded to be a sign of the equipment with the sliding parts or components being considerably worn and needing maintenance, so that the measured value indicating and abnormality determination device 14 announces it to an administrator by way of warning display, beep and/or light. Time interval of the reciprocal movements of the piston 2, which may vary depending upon, for example, viscosity of the fluid to be measured, is preferably on the order of several seconds or several tens of second.

Thus, according to the third embodiment, the effects and advantages can be obtained which are substantially same as those of the first and second embodiments. The third embodiment may be constructed like the variation of the second embodiment to obtain the effects and advantages similar to those of the variation of the second embodiment.

In the third embodiment which requires no communication passage unlike the second embodiment, no consideration is needed as to change of fluid flow; with the simple construction, the concentration of magnetic material in the fluid can be continuously measured with high accuracy.

Figure 5:
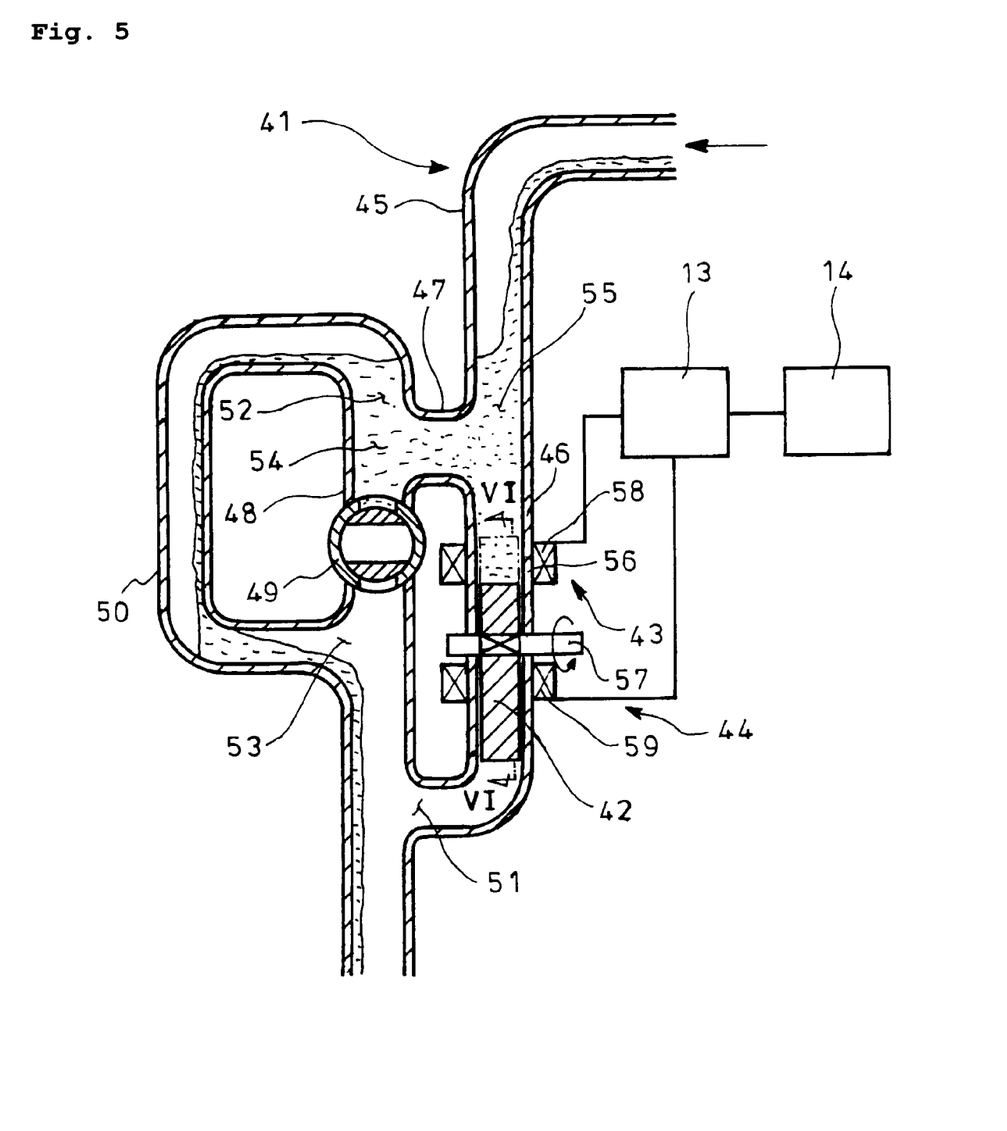
FIG. 5 is a schematic view showing a fourth embodiment of the invention.
Figure 6:
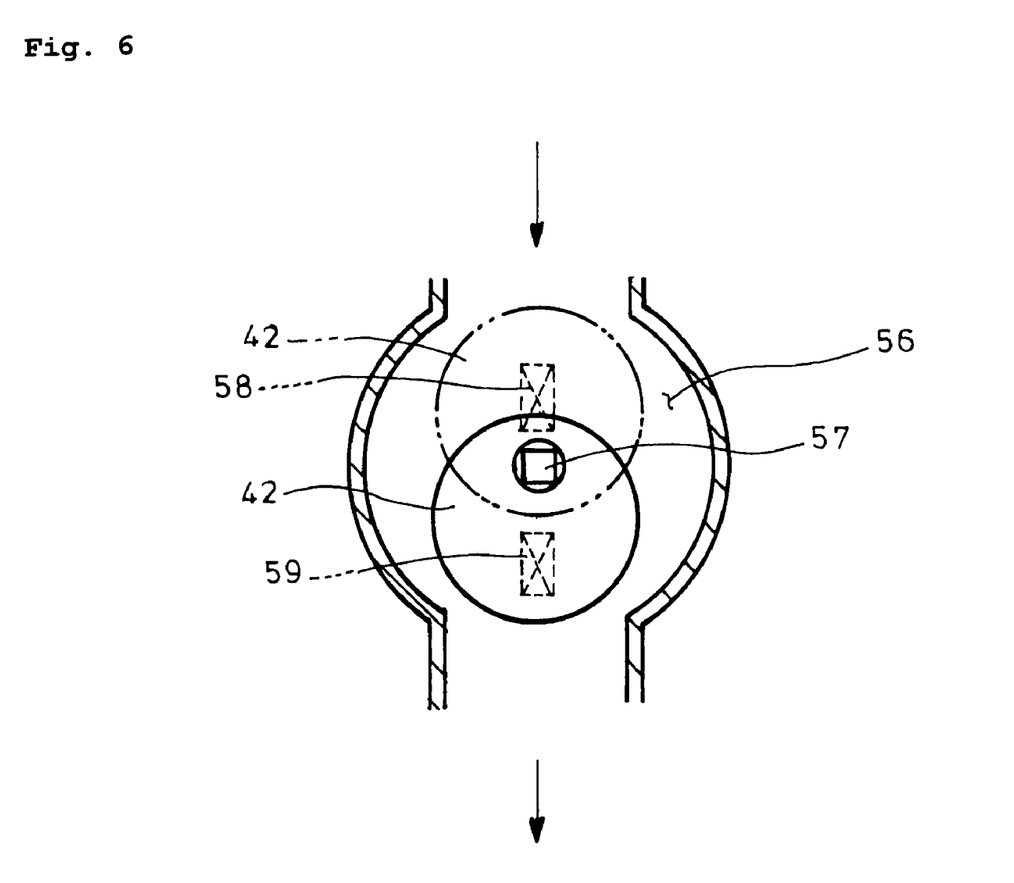
FIG. 6 is a view looking in the direction of arrows VI in FIG. 5.

Next, a conductive material concentration measuring device according to a fourth embodiment of the invention will be described. FIGS. 5 and 6 are schematic views showing the fourth embodiment of the invention. In the figures, parts similar to those in FIG. 1 are represented by the same reference numerals.

The measuring device of the fourth embodiment has a variation of the passage 1 as well as a variation of the fluid inflow/outflow guide means 2 or 11 for guiding the fluid such as lubricant including conductive material; that is, it has a passage 41 for fluid such as lubricant to which is connected a detection unit 44 with a rotator (fluid inflow/outflow guide means) 42 and detection means 43. The conductive material is not limited to magnetic material such as iron, cobalt or nickel and may be non-magnetic material such as aluminum, copper or stainless-steel, provided that it has electrical conductivity. The fluid is not limited to lubricant or drain oil and may be any, provided that it contains conductive material.

The conduit passage 41 of the fourth embodiment is for discharge of the lubricant from an equipment (not shown) with sliding parts or components. Downstream of the passage 41 are a first passage 45 extending from horizontal to vertical, a measuring passage 46 extending vertically directly from first passage 45 and having a detection unit 44, an intermediate passage 47 branched just before the measuring passage 46 and extending horizontally, a second passage 48 extending from the intermediate passage 47 further curvedly into vertical, an on-off valve 49 as shutoff means in the second passage 48 and a branch passage 50 arranged for the second passage 48 to bypass the on-off valve 49, the measuring passage 46 having a connection port 51 downstream of the on-off valve 49, the branch passage 50 having a branch port 52 on the other end of the intermediate passage 47 and a junction port 53 downstream of the on-off valve 49. The sliding parts or components are not limited to a drive piston and a drive cylinder and may be any, provided that they may slide.

The second passage 48 from a halfway position of the intermediate passage 47 to the on-off valve 49 as shutoff means provides a first pool section 54 for pooling of the old fluid or lubricant, and a portion from the first passage 45 to the measuring passage 46 provides a second pool section 55 for receiving and pooling of the new fluid or lubricant. The branch passage 50 serves to cause the overflowing lubricant from the first pool section 54 to flow downstream.

The detection unit 44 comprises a detection body (fluid inflow/outflow guide means) 56 in the form of a circular cavity in the measuring passage 46, a shaft (fluid inflow/outflow guide means) 57 passing through the detection body 56 axially of the circular cavity (or in a horizontal direction in FIG. 5), a rotator (fluid inflow/outflow guide means) 42 fixed to the shaft 57 for eccentric rotation thereof within the detection body 56, drive means (not shown) for rotating the shaft 57, upper and lower sensors 58 and 59 for the detection means 43 and arranged on an outer periphery of the detection body 56, a signal processing circuit 13 in the detection means 43 for controlling the upper and lower sensors 12 and a measured value indicating and abnormality determination device 14 connected to the circuit 13.

The rotator 42 and the shaft 57 are made from non-magnetic material and the drive means (not shown) has a drive source such as air, hydraulic or ultrasonic motor using no electromagnetic force. The reason why the drive source utilizing no electromagnetic force is used is that, if a drive source such as electric motor utilizing electromagnetic force were used, it would affect a coil, lowering detected accuracy of the concentration of conductive material.

The rotator 42 is constructed such that the rotator 42 faces the lower sensor 59 and does not face the upper sensor 58, as shown in solid lines in FIGS. 5 and 6, when it is in a position where a portion with greater eccentricity of the rotator 42 is on one side (or lower side in the figures) with respect to the shaft and that the rotator 42 faces the upper sensor 58 and does not face the lower sensor 59, as shown in imaginary lines in FIGS. 5 and 6, when it is in a position where a portion with greater eccentricity of the rotator 42 is on one side (or upper side in the figures) with respect to the shaft. The rotator 42 serves to block the inflow of the fluid into the detection body 56 when the portion with the greater eccentricity of the rotator 42 is at an inflow side (upper side in the figures).

Just like the first embodiment, the sensors 58 and 59 in the detection means 43 measure the concentration of the conduction material power through, for example, differential transformer type detection; however, the way of detection is not limited thereto and may be any, provided that it can measure a concentration of conductive material powder.

Mode of operation of the fourth embodiment according to the invention will be described.

Upon measurement of the concentration of conductive material included in the lubricant (fluid), with the portion with greater eccentricity of the rotator 42 to the shaft being preliminarily situated at the inflow side (or upper side in the figures), the on-off valve 49 in the passage 41 is closed to pool a constant amount of lubricant in the second and first pool sections 55 and 54. Whether a predetermined amount of lubricant has been pooled or not in the second pool section 55 may be determined on the basis of lapse of a predetermined time; alternatively, it may be determined on the basis of detection of the overflowing lubricant into the branch passage 50 as shown in FIG. 5; alternatively, any other determination means may be employed.

Then, the portion with the greater eccentricity of the rotator 42 to the shaft is swung into the discharge side (or lower side in the figures) to guide the lubricant in the second pool section 55 into the detection unit 44, so that the concentration of conductive material in the lubricant is measured by the sensors 58 and 59 of the detection means 43. The detection means 43 measures output signals from the sensors 58 and 59 via the signal processing circuit 13. Since the output signals from the sensors 58 and 59 vary depending on the concentration of conductive material powder in the detection unit 44, the concentration of conductive material powder is measured through functional processing of the output signals from the sensors 58 and 59 or through contrast processing using correlation of conductive material powder.

Then, by swinging the portion with great eccentricity of the rotator 42 to the shaft to the inflow side (or upper side in the figures), the lubricant in the detection unit 44 is discharged (or guided out) downwardly via the connection port 51 to discharge the accumulated bodies in the detection unit 44 and replace the lubricant in the detection unit 44.

Then, with such eccentric swinging of the rotator 42 being continued, the concentration of conductive material powder in the lubricant is continuously measured. When the concentration of conductive material powder exceeds a predetermined value, the fact is regarded to be a sign of the equipment with the sliding parts or components being considerably worn and needing maintenance, so that the measured value indicating and abnormality determination device 14 announces it to an administrator by way of warning display, beep and/or light. Time interval of the swinging motion of the rotator 42, which may vary depending on, for example, viscosity of the fluid to be measured, is preferably on the order of several seconds or several tens of seconds.

Thus, according to the fourth embodiment, the eccentric swinging or rotating of the rotator (fluid inflow/outflow guide means) 42 facilitates guide and replacement of the fluid or lubricant in the detection unit 44, so that the replacement of the lubricant in the detection unit 44 is accelerated. As a result, the concentration of conductive material powder in the fluid is continuously measured with high accuracy and accordingly abnormality of the equipment can be quickly detected. Since the abnormality of the sliding parts in the equipment can be quickly detected, maintenance can be made before the equipment suffers from serious damages. Since the concentration of conductive material powder in the fluid is detected in the detection unit 44 different in pathway from the passage 41, the detection can be prevented from being affected by disturbances such as magnetic noise, electromagnetic noise, temperature variation and electric noise.

Since the accumulated solid and other bodies are removed by swinging or rotation of the rotator 42, a periodic air blowing or mechanical removal becomes unnecessary and occurrence of further accumulation and change in measurement conditions is prevented, so that the concentration of conductive material powder in the fluid can be continuously measured with high accuracy. Even if the fluid has high viscosity, the fluid can be surely guided in a constant interval by eccentric swinging or rotation of the rotator 42, so that the concentration of conductive material powder in the fluid can be continuously measured with high accuracy. The eccentric swinging or rotation of the rotator 42 easily discharge air originally existing in the passage 41 and the detection unit 44, so that movement of the fluid becomes smooth and the concentration of conductive material powder in the fluid can be continuously measured with high accuracy.

In an equipment such as diesel engine, lubricant is fed with revolution speed and charged fuel degree as parameters; supply of the lubricant may be also controlled with the measured concentration of conductive material powder in the lubricant used as condition parameter for a drive cylinder (cylinder liner). When, in addition to measurement of the concentration of conductive material, mean is provided for measurement of an amount of drain oil, a worn amount of the equipment may be estimated so that timing for maintenance of the equipment can be properly grasped to reduce time and cost required for the maintenance.

In the fourth embodiment, when the detection unit 44 is connected to the second pool section 55 for pooling of the fluid in the passage 41 such that air is prevented from interfusing, inflow and outflow of the fluid is guided by the rotator 42 as fluid inflow/outflow guide means without interfusion of air into the detection unit 44, so that replacement of the fluid in the detection unit 44 can be easily conducted and the concentration of conductive material powder in the fluid can be continuously measured with high accuracy. Since the detection unit 44 is connected to the second pool section 55, air is prevented from interfusing by vibrations and the like of the equipment such as engine. Even if the fluid has high viscosity, the fluid can be favorably guided from the second pool section 55 for the fluid in a constant interval by eccentric swinging or rotation of the rotator 42, the concentration of conductive material powder in the fluid can be continuously measured with high accuracy.

In the fourth embodiment, when the second pool section 55 is formed in the passage 41 by the on-off valve 49 as shutoff means, the second pool section 55 is easily formed in the passage 41, so that the replacement of the fluid in the detection unit 44 can be easily conducted and the concentration of conductive material powder in the fluid can be continuously measured with high accuracy. Even if the fluid has high viscosity, the fluid can be favorably guided from the second pool section 55 for the fluid in a constant interval by swinging or rotation of the rotator 42 as fluid inflow/outflow guide means, the concentration of conductive material powder in the fluid can be continuously measured with high accuracy.

Figure 7:
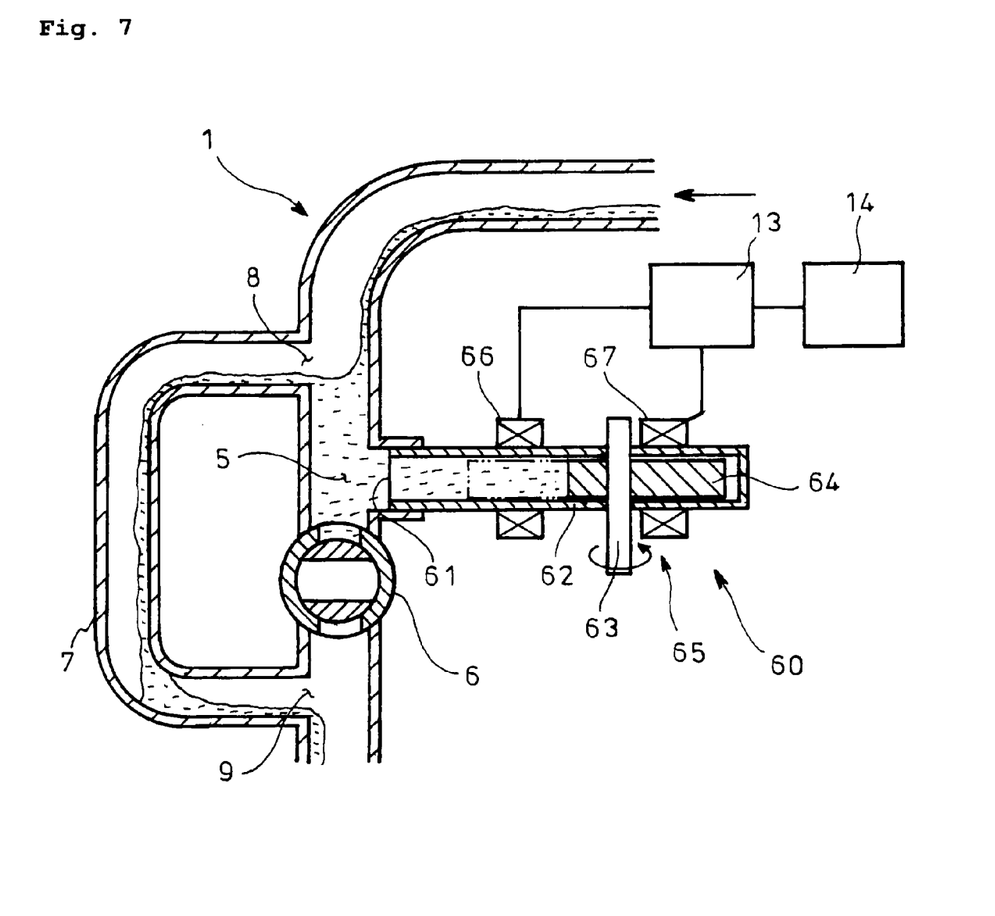
FIG. 7 is a schematic view showing a fifth embodiment of the invention.

Next, a conductive material concentration measuring device according to a fifth embodiment of the invention will be described. FIG. 7 is a schematic view showing the fifth embodiment of the invention. In the figure, parts similar to those in FIG. 1 are represented by the dame reference numerals.

In the measuring device of the fifth embodiment, connected to the conduit passage 1 for passage of fluid such as lubricant including conductive material is a detection unit 60 just like the detection unit 44 of the fourth embodiment. The conductive material is not limited to magnetic material such as iron, cobalt or nickel and may be non-magnetic material such as aluminum, copper or stainless-steel, provided that it has electrical conductivity. The fluid is not limited to lubricant or drain oil and may be any, provided that it contains conductive material.

The detection unit 60 comprises a detection body (fluid inflow/outflow guide means) 62 in the form of a circular cavity and having an opening 61 to the pool section 5 so as to be arranged for the passage 1 between the on-off valve 6 and the branch port 8, a shaft (fluid inflow/outflow guide means) 63 passing through the detection body 62 axially of the circular cavity (or in a vertical direction in FIG. 7), a rotator (fluid inflow/outflow guide means) 64 fixed to the shaft 63 for eccentric rotation thereof within the detection body 62, drive means (not shown) for rotating the shaft 63, left and right sensors 66 and 67 for the detection means 65 and arranged on an outer periphery of the detection body 62, a signal processing circuit 13 in the detection means 65 for controlling the sensors 66 and 67 and a measured value indicating and abnormality determination device 14 connected to the circuit 13.

The rotator 64 and the shaft 63 are made from non-magnetic material and the drive means (not shown) has a drive source such as air, hydraulic or ultrasonic motor using no electromagnetic force. The reason why the drive source utilizing no electromagnetic force is used is that, if a drive source such as electric motor utilizing electromagnetic force were used, it would affect a coil, lowering detected accuracy of the concentration of conductive material.

The rotator 64 is constructed such that the rotator 64 faces the right sensor 67 and does not face the left sensor as shown in solid lines in FIG. 7 when it is in a position where a portion with greater eccentricity of the rotator is on one side (or right in the figure) with respect to the shaft and that the rotator 64 faces the left sensor 66 and does not face the right sensor 67, as shown in imaginary lines in FIG. 7 when it is in a position where a portion with greater eccentricity of the rotator 64 is on one side (or left side in the figure) with respect to the shaft. The rotator 64 serves to block the inflow of the fluid into the detection body 62 when the portion with greater eccentricity of the rotator 64 to the shaft is the opening side (left in the figure).

Just like the first embodiment, the sensors 66 and 67 of the detection means 65 measures the concentration of conductive material powder through, for example, differential transformer type detection; however, they way of detection is not limited thereto and may be any, provided that it can measure a concentration of conductive material powder. Like the variation of the second embodiment, a horizontally extending pool section may be arranged to arrange the detection unit 60 above the pool section.

Mode of operation of the fifth embodiment of the invention will be described.

Upon measurement of the concentration of conductive material included in the lubricant (fluid), with the portion with greater eccentricity of the rotator 64 to the shaft being preliminarily situated at the opening side (or left in FIG. 7), the on-off valve 6 in the passage 1 is closed to pool a constant amount of lubricant in the section 5. Whether the predetermined amount of lubricant has been pooled or not in the pool section 5 may be determined on the basis of lapse of a predetermined time; alternatively, it may be determined on the basis of detection of the overflowing lubricant into the branch passage 7 as shown in FIG. 7; alternatively, any other determination means may be employed.

Then, the portion with the greater eccentricity of the rotator 64 to the shaft is swung or rotated away from the opening (right in FIG. 7) to guide the lubricant in the pool section 5 into the detection unit 60, so that the concentration of conductive material in the lubricant is measured by the sensors 66 and 67 of the detection means 65. The detection means 65 measures output signals from the sensors 66 and 67 via the signal processing circuit 13. Since the outputs from the sensors 66 and 67 vary depending on the concentration of magnetic material powder in the detection unit 60, the concentration of magnetic material powder is measured through functional processing of the output signals from the sensors 66 and 67 or through contrast processing using correlation of the concentration of magnetic material powder.

Then, by swinging or rotating the portion with great eccentricity of the rotator 64 to the shaft to the opening side (or left in FIG. 7), the lubricant in the detection unit 60 is discharged (or guided out) into the pool section 5 to discharge the accumulated bodies in the detection unit 60 and replace the lubricant in the detection unit 60 and the pool section 5.

Then, with such eccentric rotations of the rotator 64 being continued, the concentration of magnetic material powder is continuously measured. When the concentration of conductive material powder exceeds a predetermined value, the fact is regarded to be a sign of the equipment with sliding parts or components being considerably worn and needing maintenance, so that the measured value indicating and abnormality determination device 14 announces it to an administrator by way of warning display, beep and/or light. Time interval of the eccentric rotations of the rotator 64, which may vary depending on, for example, viscosity of the fluid to be measured, is preferably on the order of several seconds or several tens of seconds.

Thus, according to the fifth embodiment, the effects and advantages can be obtained which are substantially same as those of the first and fourth embodiments. The fifth embodiment may be constructed like the variation of the second embodiment to obtain the effects and advantages similar to those of the variation of the second embodiment.

In the fifth embodiment, the detection unit 60 with the rotator (fluid inflow/outflow guide means) 64 and the detection means 65 may be combined with the passage 21 or 31 of the second or third embodiment; then, obtainable are the effects and advantages substantially similar to those in the second or third embodiment.

It is to be understood that a conductive material concentration measuring device and a magnetic material concentration measuring device according to the invention is not limited to the above embodiments and that various changes and modifications may be made without departing from the scope of the invention. For example, the passages are not limited to those in the embodiments and may be other passages extending horizontally or slantly, provided that they can bring about the same effects and advantages. The fluid is not limited to lubricant and may be other oil, aqueous solution, water or powder. The shutoff means is not limited to the on-off valve and may be a stopper or a passage changeover structure.

INDUSTRIAL APPLICABILITY

A magnetic material concentration measuring device according to the invention can measure a concentration of magnetic material produced due to sliding of parts. A conductive material concentration measuring device according to the invention can measure a concentration of conductive material produced due to sliding of parts.

The invention claimed is:

1. A conductive material concentration measuring device comprising a detection unit with detection means and fluid inflow/outflow guide means, said detection unit being provided for a pool section for pooling of fluid with conductive material, said pool section comprising first and second pool sections for pooling of old and new fluids, respectively, said detection unit being connected to the second pool section, said detection unit guiding inflow and outflow of the fluid through said fluid inflow/outflow guide means and detecting a concentration of conductive material through said detection means.

2. A conductive material concentration measuring device comprising a detection unit with detection means and fluid inflow/outflow guide means, said detection unit being provided for a pool section for pooling of fluid with conductive material so as to prevent air from interfusing, said pool section comprising first and second sections for pooling of old and new fluids, respectively, said detection unit being connected to the second pool section, said detection unit guiding inflow and outflow of the fluid through said fluid inflow/outflow guide means and detecting a concentration of conductive material through said detection means.

3. A conductive material concentration measuring device comprising a detection unit with detection means and fluid inflow/outflow guide means, said detection unit being provided for a pool section for fluid with conductive material, a pool section for pooling of said fluid being formed in the passage through shutoff means, so as to prevent air from interfusing, said detection unit being connected to said pool section, said detection unit guiding inflow and outflow of the fluid through said fluid inflow/outflow guide means and detecting a concentration of conductive material through said detection means.

4. A conductive material concentration measuring device comprising a detection unit with detection means and fluid inflow/outflow guide means, said detection unit being formed in a passage for fluid with conductive material, a pool section for pooling of said fluid being formed in the passage through shutoff means, said pool section comprising first and second sections for pooling of old and new fluids, respectively, said detection unit being connected to the second pool section, said detection unit guiding inflow and outflow of the fluid through said fluid inflow/outflow guide means and detecting a concentration of conductive material through said detection means.

5. A conductive material concentration measuring device comprising a detection unit with detection means and fluid inflow/outflow guide means, said detection unit being formed in a passage for fluid with conductive material, a pool section for pooling of said fluid being formed in the passage through shutoff means so as to prevent air from interfusing, said pool section comprising first and second sections for pooling of old and new fluids, respectively, said detection unit being connected to the second pool section, said detection unit guiding inflow and outflow of the fluid through said fluid inflow/outflow guide means and detecting a concentration of conductive material through said detection means.

6. A magnetic material concentration measuring device comprising a detection unit with detection means and a piston, said detection unit being connected to a passage for fluid with magnetic material, said detection unit guiding inflow and outflow of the fluid caused to flow into and out of the detection unit by said piston, and detecting a concentration of the magnetic material via said detection means.

7. A magnetic material concentration measuring device as claimed in claim 6, wherein said pool section comprises first and second pool sections for pooling of old and new fluids, respectively, said detection unit being connected to the second pool section.

8. A magnetic material concentration measuring device as claimed in claim 7, wherein said pool section is formed in the passage through shutoff means.

9. A magnetic material concentration measuring device as claimed in claim 6, wherein said detection unit is connected to the pool section such that air is prevented from interfusing.

10. A magnetic material concentration measuring device as claimed in claim 9, wherein said pool section is formed in the passage through shutoff means.

11. A magnetic material concentration measuring device as claimed in claim 9, wherein said pool section comprises first and second pool sections for pooling of old and new fluids, respectively, said detection unit being connected to the second pool section.

12. A magnetic material concentration measuring device as claimed in claim 11, wherein said pool section is formed in the passage through shutoff means.

* * * * *